United States Patent [19]

Burns

[11] Patent Number: 5,084,184

[45] Date of Patent: Jan. 28, 1992

[54] POSITIVE FOCUSING IN A MAGNETICALLY STABILIZED FLUIDIZED BED

[75] Inventor: Mark A. Burns, Ann Arbor, Mich.

[73] Assignee: Exxon Chemical Patents Inc., Linden, N.J.

[21] Appl. No.: 667,622

[22] Filed: Mar. 11, 1991

[51] Int. Cl.$^5$ .............................................. B01D 15/08
[52] U.S. Cl. .......................................... 210/656; 55/3; 55/18; 55/19; 55/20; 55/67; 55/100; 55/386; 55/390; 210/198.2; 210/222; 210/661; 210/695
[58] Field of Search ............ 210/656, 661, 695, 198.2, 210/222, 635; 55/3, 4, 18–20, 22, 60, 67, 77, 100, 386, 390

[56] References Cited

U.S. PATENT DOCUMENTS

| | | | |
|---|---|---|---|
| 4,283,204 | 8/1981 | Savage | 55/3 |
| 4,668,379 | 5/1987 | Rosenweig et al. | 55/3 |
| 4,780,113 | 10/1988 | Koslow | 55/3 |

OTHER PUBLICATIONS

Dr. Mark Burns' Thesis Entitled, "Continuous Affinity Chromatography Using a Magnetically Stabilized Fluidized Bed", 1986, University Microfilms Inc., Ann Arbor, Michigan.

*Primary Examiner*—Robert A. Dawson
*Assistant Examiner*—Sun Uk Kim

[57] ABSTRACT

A process of positive focusing of a component of a feedstream in a magnetically stabilized fluidized bed which comprises: (a) providing in a column a bed of magnetizable adsorbent solids for which the component has an affinity, the bed descending countercurrently to an ascending flow through the bed of a fluidizing medium which enters the column at a fluidizing medium entry point, and the bed being stabilized by a magnetic means of sufficient strength to suppress solids backmixing and to preserve staging therein; (b) introducing the feedstream into the column through at least one feedpoint which is spaced above the fluidizing medium entry point, the feedstream and the fluidizing medium together comprising a fluid phase within the column; and (c) adjusting conditions such that they are effective to result in concentration of the component within at least one positive focusing zone in the column wherein above the zone the velocity of the component is less than zero and below the zone the velocity of the component is greater than zero. The velocity of the desired component is controlled by adjusting conditions of the fluid phase above and below the positive focusing zone, e.g., temperature, salt concentration, pH and/or organic concentration.

14 Claims, 2 Drawing Sheets

POSITIVE FOCUSING IN A MAGNETICALLY STABILIZED FLUIDIZED BED

The present invention relates to a novel process of separating and concentrating a component from a feedstream in a magnetically stabilized fluidized bed chromatography column using positive focusing. Separation occurs by adjusting conditions within the chromatography column so as to concentrate the desired component within at least one positive focusing zone. The desired component is directed into the positive focusing zone by controlling the operating conditions such that above the zone the velocity of the component is less than zero and below the zone the velocity of the component is greater than zero.

BACKGROUND OF THE INVENTION

Magnetically stabilized fluidized bed chromatography columns have been used to concentrate and separate various substances, e.g., chemicals and pharmaceuticals. See U.S. Pat. No. 4,780,113 (Koslow), issued Oct. 25, 1988, which is incorporated herein by reference. The Koslow patent is directed to an isomobility focusing process of one component from a multi-component feedstream using a magnetically stabilized fluidized bed. The feedstream is introduced into the magnetically stabilized bed of magnetizable solids for which the component to be separated has an affinity, the solids descending countercurrently to an ascending flow of a fluidizing medium, the feedstream and the fluidizing medium together comprising a fluid phase within the column, under conditions wherein the component is concentrated within at least one isomobility focusing zone within the column. The isomobility focusing zone is the region within the column where an equilibrium is maintained between the velocity of the component in the fluid phase and the velocity of the component on the solid phase. Conditions of temperature, pH or salt concentration are adjusted such that the desired component is purified and concentrated as it is introduced into the column. The desired component is removed from the column as a sidestream or by elution with an eluent.

By varying certain process parameters, it is possible to establish conditions such that the movement of a given component of the feedstream in the fluid phase is equal to the movement of that component on the solid phase. If the two phases are moving in opposite directions, the component will have no net velocity, i.e., its movement in one direction with one phase being equal and opposite to its movement with the other phase.

The isomobility focusing process is demonstrated in FIG. 2, attached hereto. FIG. 2 depicts a three component feedstream wherein component P has an affinity to magnetizable adsorbent solids having a velocity less than zero, (i.e., a descending flow). The component's affinity to the solids is carefully balanced against the upflowing velocity of the fluidizing medium which has a velocity greater than zero, (i.e., an ascending flow), such that the velocity of component P is approximately zero. The velocities of components A and B are less than zero and greater than zero, respectively. Concentration of component P results due to the different velocities of the individual components within the column. That is, due to their net velocities components A and B will move out of the isomobility zone, whereas component P having a net velocity of approximately zero will remain within the isomobility zone.

Experience has shown that isomobility focusing (IMF) in a magnetically stabilized fluidized bed chromatography column has the following disadvantages: (1) the process results in diffusion tailings of the selected component outside the isomobility focusing zone which necessitates the use a longer chromatography column and shorter operating periods; and (2) isomobility focusing is somewhat difficult to control, (i.e., IMF requires continual adjustment of the conditions to maintain an equilibrium between the velocity of the component in the ascending fluid phase and the velocity of the component on the descending solid phase).

The present inventor has developed a process which makes use of the enhanced capabilities of a magnetically stabilized fluidized bed chromatography column and also overcomes the aforementioned disadvantages pertaining to isomobility focusing. In this regard, the present inventor has developed a process which separates and concentrates a desired component of a feedstream in a magnetically stabilized fluidized bed chromatography column by means of positive focusing.

Positive focusing provides the following advantages over isomobility focusing: (1) elimination of diffusion tailings, i.e., it actively resists diffusion of the selected component from the positive focusing zone; (2) permits the use of a much shorter column than isomobility focusing; (3) extends the system's operational period; and (4) easier to control.

Multi-component separations by means of a continuous chromatography column using sidestream withdrawal is discussed in Dr. Mark Burns' thesis, entitled "Continuous Affinity Chromatography Using a Magnetically Stabilized Fluidized Bed", *University Microfilms Inc.*, Ann Arbor, Mich. In accordance with the aforementioned thesis, a sidestream from the column is used to adjust the liquid flow in chromatography column and balance a component at the entrance of the sidestream. This balancing of components is accomplished by the following principle. In the lower section of the column, the liquid flow rate is greater than the solids flow rate and the desired component tends to travel up the column. Above the sidestream, the liquid flow rate is less than the solids flow rate and the protein will travel down the column with the solids phase. Thus, the net effect is that the desired component is focused at the withdrawal point of the sidestream.

The problem with a sidestream withdrawal system is that since the feedstream is injected adjacent to the sidestream withdrawal, the other components to be separated within the system must travel past the sidestream withdrawal port to be removed at the top or bottom of the column. Thus, as the solute moves up through the column, over 25 percent of the other components are removed via the sidestream withdrawal port. Such contamination cannot be avoided in this type of sidestream withdrawal system, since at least one component in the multi-component system would have to travel past or through two or more ports. Furthermore, a system controlled by adjusting the sidestream withdrawal rate is incapable of acting in a batch mode and results in the production of highly contaminated separated components.

The present inventor has discovered that the use of positive focusing in place of isomobility focusing in the separation and concentration of a component from a feedstream in a magnetically stabilized fluidized bed chromatography column greatly enhances the overall performance of the system. Furthermore, the present invention produces positive focusing by adjusting various operating conditions such that the desired component is separated and concentrated within a positive focusing zone, wherein above the zone the velocity of the component is less than zero and below the zone the velocity of the component is greater than zero.

The present invention also provides many additional advantages which shall become apparent as described below.

SUMMARY OF THE INVENTION

A process of positive focusing of a component of a feedstream in a magnetically stabilized fluidized bed which comprises: (a) providing in a column a bed of magnetizable adsorbent solids for which the component has an affinity, the bed descending countercurrently to an ascending flow through the bed of a fluidizing medium which enters the column at a fluidizing medium entry point, and the bed being stabilized by a magnetic means of sufficient strength to suppress solids backmixing and to preserve staging therein; (b) introducing the feedstream into the column through at least one feedpoint which is spaced above the fluidizing medium entry point, the feedstream and the fluidizing medium together comprising a fluid phase within the column; and (c) adjusting conditions such that they are effective to result in concentration of the component within at least one positive focusing zone in the column wherein above the zone the velocity of the component is less than zero and below the zone the velocity of the component is greater than zero. The velocity of the desired component is controlled by adjusting the operating conditions of the fluid phase above and below the positive focusing zone, e.g., temperature, salt concentration, pH and/or organic concentration.

The present invention provides an improved process for concentrating and separating a component of a feedstream in a controllably transported countercurrent flow magnetically stabilized fluidized bed. According to this process, the component of the feedstream or feed mixture which is sought to be isolated accumulates within a defined region in the column and the other components of the mixture pass from the column either with the exiting solids or with the fluid phase.

By varying certain process parameters, it is possible to establish conditions such that the velocity of the desired component above the positive focusing zone is less than zero and below the positive focusing zone is greater than zero.

Other and further objects, advantages and features of the present invention will be understood by reference to the following specification in conjunction with the annexed drawings, wherein like parts have been given like numbers.

DESCRIPTION OF THE PREFERRED EMBODIMENTS

Figure 1:
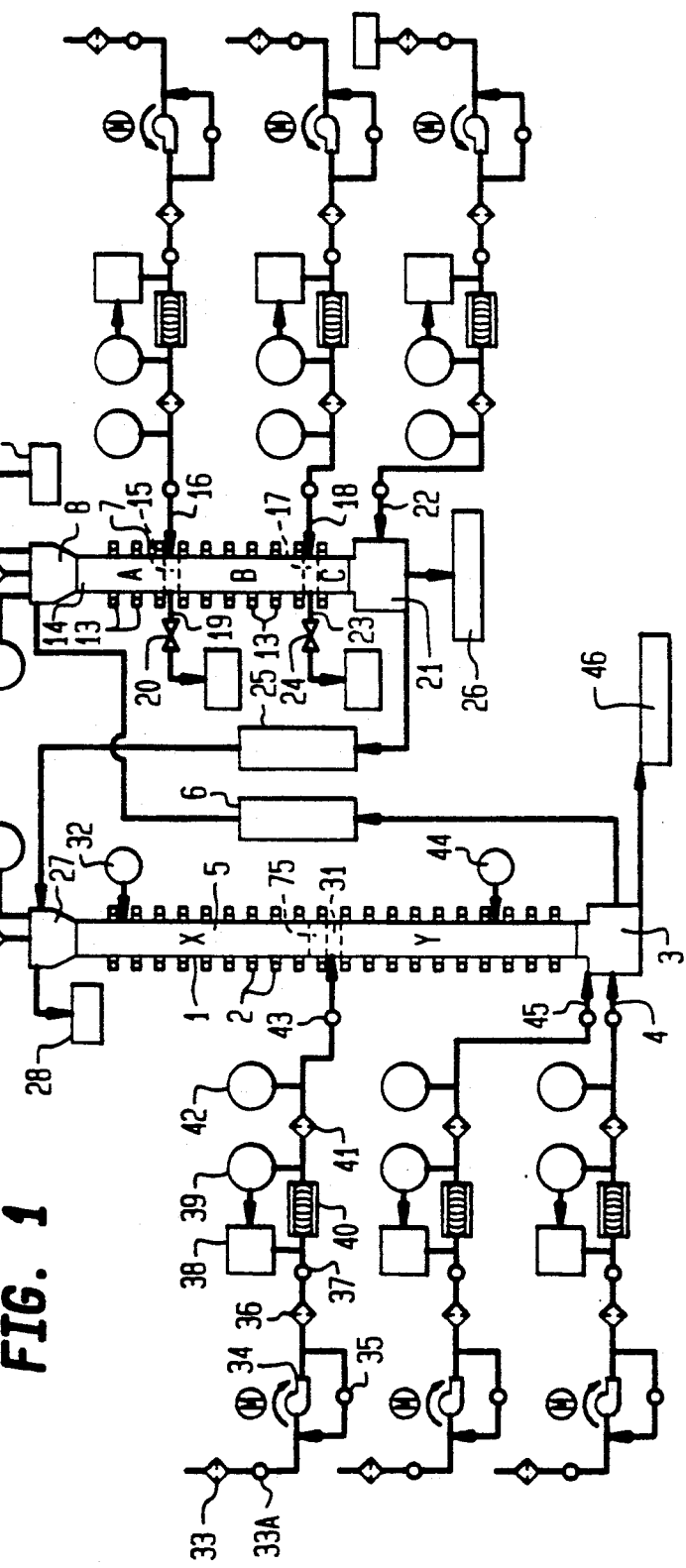
FIG. 1 is a schematic representation of a magnetically stabilized fluidized bed chromatography system used in accordance with the present invention.

The process of selectively concentrating and separating a component of a mixture in a controllably transported magnetically stabilized fluidized bed is hereinafter referred to as "positive focusing", because it results in the concentration of that component as a result of controlling the velocity of the component above and below a positive focusing zone so that the component is always directed towards that zone.

The positive focusing process can be particularly useful in a variety of specialty chemical and pharmaceutical separations requiring relatively large numbers of theoretical plates to achieve the desired level of purification or when handling feedstocks having a relatively low concentration of the desired product and requiring a significant increase in the concentration and purity of the product.

The positive focusing process can be used to carry out separations of both inorganic and organic compounds in the liquid or gas phase.

Organic compounds which can be separated include fine chemicals, specialty aromatics and paraffins, botanicals and extracts from natural materials, synthetic organic mixtures, biomolecules, fermentation products such as pharmaceuticals, hormones, oils, enzymes and proteins, specialized polysaccharides, amino acids, flavorings, pigments and lubricants.

Inorganic compounds include the salts of metals such as gold, silver, or copper which can be separated from leachates by employing ion-exchange resins in the process. The concentrated product can be reprocessed through electrowinning or direct chemical reduction.

The initial choice of adsorbent and fluidizing medium will have a direct impact on the conditions required to establish positive focusing conditions. The product molecule preferably has an affinity for the adsorbent such that the product molecule is neither irreversibly bound to the adsorbent (which will result in the product escaping from the column with the adsorbent flow) nor unadsorbed (resulting in the product molecule passing from the column with the fluid phase). The required affinity can be within a broad acceptable range sufficient to provide a reasonably high mobility of the product molecule within the chromatography column.

Chemical or physical properties of the fluid phase such as temperature, salt concentration, pH and/or organic concentration can be adjusted to achieve positive focusing. For example, macromolecular biochemicals are generally charged but this charge will vary with the pH of the buffer. If, for example, an anion-exchange resin is used as the chromatographic medium, then the affinity of different biomolecules for this medium will decline as their negative charge is neutralized at low pH. Therefore, if the pH is controlled above the positive focusing zone such that the component exhibits a net velocity of less than zero and controlled below the positive focusing zone such that the component exhibits a net velocity of greater than zero, then it is possible to cause a selected component of a feedstream to concentrate within the positive focusing zone of the column without substantial diffusion. (See FIG. 3).

Additionally or in the alternative, the column can be designed to include heating elements that can be used to adjust the temperature of different sections of the column. When the adsorption of the desired component on the solid phase is exothermic, heating of the column results in a reduction in the adsorption capacity of the adsorbent for the component. Under these conditions, the upper zone of the chromatography column having a higher fluid velocity is operated at a lower temperature to obtain higher solid phase adsorption, whereby the desired component exhibits above the positive focusing zone a net velocity of less than zero. The lower zone of the chromatography column having a lower fluid velocity is operated at a higher temperature to obtain lower affinity of the component for the adsorbent, whereby the desired component exhibits below the positive focusing zone a net velocity of greater than zero.

Common salts can also be used to depress the adsorption of charged chemical species on charged adsorbents. The presence of salts in solution surrounding an ion-exchange resin results in a decline in adsorption capacity and significant changes in the ionic double layer surrounding the solid phase. Addition or dilution of salts dissolved within the fluid phase can significantly alter the affinity of a charged product molecule for the adsorbent and thus facilitate positive focusing conditions in the column. Therefore, the salt concentration above the positive focusing zone is reduced to obtain a component with a velocity less than zero, while the salt concentration below the positive focusing zone is increased to obtain a component with a velocity greater than zero.

It is also possible to adjust the organic concentration of the fluid phase such that they differ in the regions of the chromatography column above and below the positive focusing zone to promote positive focusing of the component similar to systems controlled by adjustments to pH, temperature and salt concentration.

It is also possible to promote or assist positive focusing by controlling the flow rate of sidestream withdrawal, in conjunction with control of the operating conditions, such that above the positive focusing zone the velocity of the desired component is less than zero and the velocity of the fluidizing medium is less than the velocity of the magnetizable adsorbent solids, and below the positive focusing zone the velocity of the desired component is greater than zero and the velocity of the fluidizing medium is greater than the velocity of the magnetizable adsorbent solids.

According to the process of this invention, a bed of magnetizable adsorbent solids which is fluidized by the flow of a fluidizing medium descends countercurrently to the flow of the fluidizing medium. Solids are added to the top of the column and removed from the bottom of the column. A feedstream is injected at a feedpoint along the column, the fluidizing medium and the feedstream together comprising a fluid phase within the column. The column is maintained in a magnetic field, preferably axial in direction, wherein field strength is sufficient to maintain a fixed relationship between the individual particles within the column and to minimize backmixing.

In one embodiment of the process, the feedstream is injected into the system and the process is operated over an extended period to collect product within the column and discard impurities. Thereafter, the feed is discontinued and the product is recovered by injection of an eluent to force complete elution of the product captured within the positive focusing column.

In another embodiment of the process, the feedstream is injected into the system and the process operated over a period of time to collect product and discard impurities. The feed is then discontinued, but the fluidization of the system is continued, to force residual impurities from the column prior to product recovery. Product is then recovered by means of a stepwise change in operating conditions by means of injection of eluent to force complete elution of the product from the column.

In another embodiment of the process, the feedstream is injected into the system and operation of the process is sustained for the time sufficient to collect product and discard impurities. The feed is then discontinued. Product is recovered through a gradient elution of the product within the column to obtain increased resolution of product from impurities during the elution step.

In a further embodiment of the system, the feedstream is injected and the process operated over a period of time sufficient to collect product and discard impurities. The feed is then discontinued while fluidization is maintained to permit residual impurities to pass from the column prior to product recovery. The product is then recovered through gradient elution of the product from the column.

In an even further embodiment of the process of the present invention, the process is operated continuously, feed being injected into the system and impurities being passed from the ends of the column, with continuous or semi-continuous recovery of product by means of one or more sidestreams located near the feedpoint of the column to achieve continuous separation and recovery of product. Sidestream withdrawal is maintained at a constant rate so as not to interfere with the positive focusing of a selected component due to adjustment of the operating parameters.

The particular adsorbent employed can vary broadly and will depend upon the components of the mixture to be separated. Inorganic or organic adsorbents may be used.

Suitable adsorbents include activated aluminas, silica and silica gels, molecular sieves of carbon or zeolite, reverse phase chromatography media, exclusion chromatography media, ion-exchange chromatography media, affinity chromatography media, gel ion-exchange media, adsorbent celluloses or alginates of natural or man-made origins, or other adsorbents routinely used in high performance liquid chromatography, liquid chromatography, or gas chromatography applications. Most of these adsorbents are readily available in the commercial market or may be synthesized without elaborate techniques.

Adsorbents which are particularly useful in the present invention are ion-exchange resins, including cation-exchange resins exchanged with benzene sulfonic acid, carboxylic acid, or phosphoric acid, and strongly or weakly basic anion-exchange resins.

The term "magnetizable adsorbent solids" as used herein contemplates that the adsorbent may be admixed and/or composited with the magnetizable particles. For a detailed discussion of magnetizable adsorbent solids and magnetically stabilized fluidized beds see U.S. Pat. No. 4,780,113 (Koslow), issued Oct. 25, 1988, which is incorporated herein by reference.

The fluidizing medium may be gaseous or liquid. For example, a buffer solution is preferred for separating biomolecules.

Figure 3:
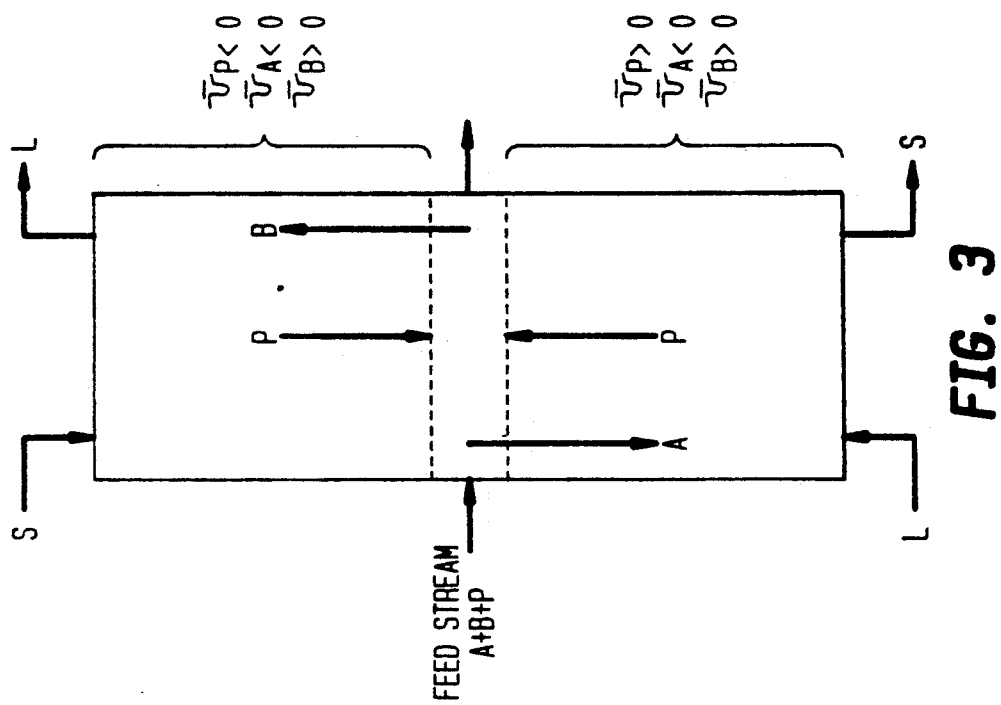
FIG. 3 is a schematic representation of a magnetically stabilized fluidized bed chromatography column using positive focusing to separate and concentrate component P in a positive focusing zone, wherein positive focusing is controlled by adjusting operating conditions such that the velocity of component P above the positive focusing zone is less than zero and the velocity of component P below the positive focusing zone is greater than zero.
Figure 2:
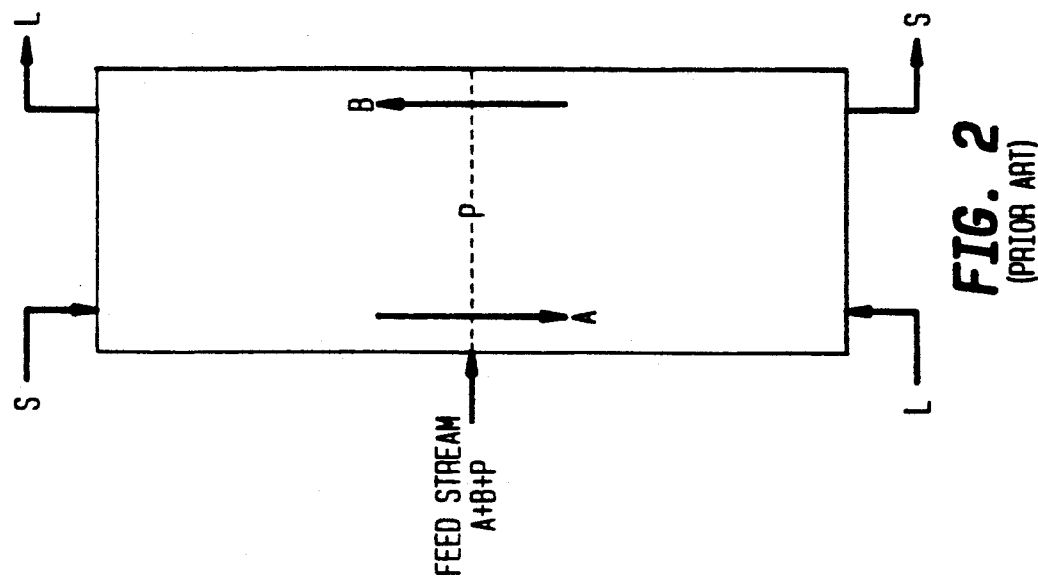
FIG. 2 is a schematic representation of a conventional magnetically stabilized fluidized bed chromatography column using isomobility focusing to separate and concentrate component P.

FIGS. 1 and 3 illustrate a preferred embodiment of the process of this invention utilizing positive focusing through pH controls and the use of a buffer as the fluidizing medium, and also illustrate in a more general sense the operation of the positive focusing system. The main production column 1 is surrounded by electromagnets 2 suspended on a supporting scaffolding (not shown). At the bottom of the production column is a distributor 3 that serves to uniformly inject a fluidizing medium such as a buffer solution supplied from buffer supply line 4 to fluidize the magnetically stabilized particles 5 in the production column. The adsorbent solids traveling downward through the production column by gravity pass into the distributor where they are ejected via the consumed adsorbent eductor 6 to the regeneration column 7. A solids/liquid separator 8 is located at the top of the regeneration column and consists of an expanded region of the column where the liquid flow velocity is reduced and the adsorbent particles which have passed to the regeneration column drop into the regeneration column by their own weight. This solids/liquid separator located on the top of the regeneration column is equipped with the vent filter 9 to exhaust entrained air and to prevent pressurization of the system. Fluid used to transport the adsorbent from the production column to the regeneration column overflows from the liquid/solids separator and is sent to waste via the waste eluent discharge line 10, which is equipped with a shut-off valve 11. The liquid height within the regeneration column is monitored using a fluid level sensor 12.

The regeneration column is surrounded by electromagnets 13 in a manner similar to the production column, and particles 14 moving through the regeneration column are magnetically stabilized. The regeneration column is separated into three operating zones by three distributors. Zone A at the top of the regeneration column lies above distributor 15. This distributor facilitates injection of eluent into the column from an eluent supply line 16. The eluent flows counter to the downward flow of adsorbent particles in zone A and acts to remove chemicals adsorbed on the adsorbent during its previous use in the production column. The eluent passes from the regeneration column into the solids/liquid separator at the top of the regeneration column and is sent to waste via the waste eluent discharge line. The adsorbent particles exit zone A through distributor 15 and move downward into zone B, which lies below distributor 15 and above distributor 17. Distributor 17 injects deionized (DI) water supplied from DI water line 18. The DI water flows upward against the flow of adsorbent particles and removes the eluent used to clean the adsorbent particles. The DI water flows upward to distributor 15 where it is discharged via the waste DI water discharge line 19 equipped with a shut-off valve 20.

The adsorbent particles then enter zone C at the bottom of the regeneration column, which lies between distributor 17 and distributor 21 located at the bottom of the regeneration column. Distributor 21 serves to introduce buffer supplied via buffer supply line 22, which is used to bring the adsorbent into equilibrium with the conditions existing within the production column. Buffer rises through zone C against the downward regeneration column via the waste buffer discharge line 23 equipped with a shut-off valve 24. Distributor 21 is connected to the regeneration resin eductor 25, which is used to recycle the adsorbent particles from the regeneration column back to the production column. Distributor 21 is also equipped with an adsorbent drain port 26 for removal of spent adsorbent.

Adsorbent particles recycled from the regeneration column return to a solids/liquid separator 27 located at the top of the production column. Solids/liquid separator 27 serves to allow the recycled particles to fall into the production column and allows the fluid used to transport the particles from the regeneration column to be sent to waste discharge 28. The solids/liquid separator is equipped with a vent filter 29 to prevent pressurization of the column and to allow accumulated air to escape. The liquid height is monitored by the level sensor 30 also located on the solids/liquid separator.

Adsorbent particles entering the production column pass into zone X located at the top of the production column and situated between feed distributor 31 located approximately at the midpoint of the production column and the solids/liquid separator located at the top of the production column. The temperature of the materials within zone X of the production column is monitored using a temperature sensor 32.

A feedstream containing a chemical specie to be separated and purified enters the system through filter 33 and check valve 33A that provides protection to motor-pump 34, which is equipped with a bypass loop and check valve 35. The feedstream is then pumped through a prefilter 36, which is used to control gross contamination in the system. The feedstream then passes through a check valve 37 and the outlet of a pH-control metering pump assembly 38. The pH of the feedstream must be carefully adjusted to control the affinity of the chemical specie being separated from the adsorbent particles in zone X such that the chemical specie which are to be directed into positive focusing zone 75 have a velocity in zone X which is less than zero, i.e., a net downward flow in the production column. Similarly, the pH of the buffer solution which enter the production column via buffer supply line 4 must be carefully adjusted to control the affinity of the chemical specie being separated from the adsorbent particles in zone Y such that the chemical specie which is to be directed into positive focusing zone 75 have a velocity in zone Y which is greater than zero, i.e., a net upward flow in the production column.

The pH control is achieved by placing a pH probe 39 in the feed line downstream of an in-line static mixer 40. An electronic feedback loop is used to control the addition of a pH adjustment solution (acid or base, as appropriate) that is injected into the feedstream by the pH control assembly. The feedstream then passes through a final, sterilization-grade filter 41, which is used in pharmaceutical applications to maintain the sterile conditions within the production system through the removal of microorganisms. The pH adjustment solution is added in a similar manner to buffer supply line 4 to control the pH in zone Y.

It is contemplated by the present invention that other conditions such as temperature, salt concentration and organic concentration could be adjusted either separately or in conjunction with each other and/or the pH of the fluidizing medium to accomplish positive focusing of the selected chemical specie.

The flow of feed into the system is monitored using a flow meter 42 that accurately controls the flow of feed into the production column through a feedback control system (not shown) to the speed controller controlling motor-pump 34. The feed then enters the production column at feed distributor 31 through a final check valve 43.

The feedstream combines with the buffer flow arriving from zone Y of the production column. Zone Y lies between the feed distributor 31 and distributor 3 located at the bottom of the production column. The temperature in zone Y is monitored by temperature sensor 44.

Buffer is supplied to zone Y via distributor 3, which allows fluids to rise through zone Y in countercurrent flow against the flow of magnetically stabilized adsorbent particles moving downward through zone Y. During the separation of a given chemical specie, buffer flow is adjusted against the flow of the adsorbent particles to achieve a balance of velocities for the given desired chemical component. This balance is maintained in zones X and Y through the adjustment of the affinity of the chemical specie being separated by the adjustment of at least one of the operating conditions, i.e., temperature, pH, salt concentration and/or organic concentration, in zone X such that the chemical specie contained within zone X has a velocity less than zero and in zone Y such that the chemical specie contained within zone Y has a velocity greater than zero.

The system of filters, check valves, pH controllers flow monitors and controls, and in-line mixers used for the injection of feed into the production column is replicated for the controlled injection of all fluids into the production and regeneration columns. Distributor 3 is equipped with an adsorbent drain port 46.

When sufficient time has elapsed to achieve the desired degree of purity, the product is recovered by either continuous sidestream withdrawal, semi-continuous sidestream withdrawal, or displacement of the product from the system using an eluent which is injected into the production column via eluent supply line 45. The eluent is typically a solution of high or low pH, a salt solution, a mixture of water and an organic material such as isopropyl alcohol or other eluents with a demonstrated capacity to effectively displace the product from the chosen adsorbent. When eluent is supplied to distributor 3 of the production column for product recovery, buffer flow is halted and the product is displaced upward through the column and exits the production column via waste discharge line 28. During this portion of the cycle, flow emerging from line 28 is diverted to a product recovery tank (not shown) or an alternative product receiving point.

While I have shown and described several embodiments in accordance with my invention, it is to be clearly understood that the same are susceptible to numerous changes apparent to one skilled in the art. Therefore, I do not wish to be limited to the details shown and described but intend to show all changes and modifications which come within the scope of the appended claims.

What is claimed is:

1. A process of positive focusing of a component of a feedstream in a magnetically stabilized fluidized bed which comprises:
   a. providing in a column a bed of magnetizable adsorbent solids for which said component has an affinity, said bed descending countercurrently to an ascending flow through the bed of a fluidizing medium which enters the column at a fluidizing medium entry point, and said bed being stabilized by a magnetic means of sufficient strength to suppress solids backmixing and to preserve staging therein;
   b. introducing the feedstream into the column through at least one feedpoint which is spaced above the fluidizing medium entry point, the feedstream and the fluidizing medium together comprising a fluid phase within the column; and
   c. adjusting conditions such that they are effective to result in concentration of said component within at least one positive focusing zone in the column wherein above said zone the velocity of said component is less than zero and below said zone the velocity of said component is greater than zero.

2. A positive focusing process for separating at least one component of a multi-component feedstream which process comprises:
   a. providing in a column a bed of magnetizable adsorbent solids for which said one component has an affinity, said bed descending countercurrently to an ascending flow through the bed of a fluidizing medium which enters the column at a fluidizing medium entry point, and said bed being stabilized by a magnetic means of sufficient strength to suppress solids backmixing and to preserve staging therein;
   b. introducing the feedstream into the column through at least one feedpoint which is spaced above the fluidizing medium entry point, the feedstream and the fluidizing medium together comprising a fluid phase within the column;
   c. adjusting conditions such that they are effective to result in concentration of said one component within at least one positive focusing zone in the column wherein above said zone the velocity of said one component is less than zero and below said zone the velocity of said one component is greater than zero;
   d. discontinuing the introduction of the feedstream;
   e. terminating the flow of the fluidizing medium; and
   f. recovering said one component from said column.

3. A positive focusing process for separating at least one component of a multi-component feedstream which process comprises:
   a providing in a column a bed of magnetizable adsorbent solids for which said one component has an affinity, said bed descending countercurrently to an ascending flow through the bed of a fluidizing medium which enters the column at a fluidizing medium entry point, and said bed being stabilized by a magnetic means of sufficient strength to suppress solids backmixing and to preserve staging therein;
   b. introducing the feedstream into the column through at least one feedpoint which is spaced above the fluidizing medium entry point, the feedstream and the fluidizing medium together comprising a fluid phase within the column;
   c. adjusting conditions such that they are effective to result in concentration of said one component within at least one positive focusing zone in the column wherein above said zone the velocity of said one component is less than zero and below said zone the velocity of said one component is greater than zero;
   d. discontinuing the introduction of the feedstream;
   e. maintaining the flow of the fluidizing medium; and
   f. recovering said one component from said column.

4. The process according to claim 3 wherein said one component is recovered by elution from said column.

5. The process according to claim 4 wherein said one component is recovered from said column by step-wise elution.

6. The process according to claim 4 wherein said one component is recovered from said column by gradient elution.

7. A positive focusing process for separating at least one component of a multi-component feedstream which process comprises:
   a. providing in a column a bed of magnetizable adsorbent solids for which said one component has an affinity, said bed descending countercurrently to an ascending flow through the bed of a fluidizing medium which enters the column at a fluidizing medium entry point, and said bed being stabilized by a magnetic means of sufficient strength to suppress solids backmixing and to preserve staging therein;
   b. introducing the feedstream into the column through at least one feedpoint which is spaced above the fluidizing medium entry point, the feedstream and the fluidizing medium together comprising a fluid phase within the column;
   c. adjusting conditions such that they are effective to result in concentration of said one component within at least one positive focusing zone in the column wherein above said zone the velocity of said one component is less than zero and below said zone the velocity of said one component is greater than zero; and
   d. recovering said one component from said positive focusing zone.

8. The process according to claim 7 wherein said one component is recovered as a sidestream.

9. The process according to claim 8 wherein said one component is recovered continuously.

10. The process according to claim 8 wherein said one component is recovered semi-continuously.

11. The process according to claim 1, 2, 3 or 7 wherein the condition of temperature in said column is adjusted above and below said positive focusing zone to provide positive focusing of said component.

12. The process according to claim 1, 2, 3 or 7 wherein the salt concentration of said fluid phase is adjusted above and below said positive focusing zone to provide positive focusing of said component.

13. The process according to claim 1, 2, 3 or 7 wherein the condition of pH in said column is adjusted above and below said positive focusing zone to provide positive focusing of said component.

14. The process according to claim 1, 2, 3 or 7 wherein the organic concentration in said fluid phase is adjusted above and below said positive focusing zone to provide positive focusing of said component.

* * * * *